US008670832B2

(12) United States Patent
Raykhman (10) Patent No.: US 8,670,832 B2
(45) Date of Patent: Mar. 11, 2014

(54) SYSTEM AND METHODS FOR PRODUCING AND DELIVERING ELECTRICAL IMPULSES

(76) Inventor: Igor Raykhman, Chicago, IL (US)

(*) Notice: Subject to any disclaimer, the term of this patent is extended or adjusted under 35 U.S.C. 154(b) by 223 days.

(21) Appl. No.: 13/207,257

(22) Filed: Aug. 10, 2011

(65) Prior Publication Data

US 2012/0209354 A1 Aug. 16, 2012

Related U.S. Application Data

(60) Provisional application No. 61/372,407, filed on Aug. 10, 2010, provisional application No. 61/372,356, filed on Aug. 10, 2010.

(51) Int. Cl.
*A61N 1/40* (2006.01)

(52) U.S. Cl.
USPC .......................................................... 607/46

(58) Field of Classification Search
USPC .......................................................... 607/100
See application file for complete search history.

(56) References Cited

U.S. PATENT DOCUMENTS

| 4,977,895 A | 12/1990 | Tannenbaum |
| 5,109,847 A | 5/1992 | Liss et al. |
| 5,385,150 A | 1/1995 | Ishikawa |
| 5,957,951 A | 9/1999 | Cazaux et al. |
| 6,246,912 B1 * | 6/2001 | Sluijter et al. ................ 607/100 |
| 6,285,905 B1 | 9/2001 | Chiang et al. |
| 6,735,469 B2 | 5/2004 | Lee et al. |
| 7,200,444 B2 | 4/2007 | Gavronsky et al. |
| 2007/0276449 A1 | 11/2007 | Gunter et al. |
| 2010/0013569 A1 * | 1/2010 | Torres Escajadillo et al. ............................ 332/109 |
| 2010/0298863 A1 | 11/2010 | Hindinger et al. |

* cited by examiner

*Primary Examiner* — Carl H Layno
*Assistant Examiner* — Jon Eric C Morales
(74) *Attorney, Agent, or Firm* — Valauskas Corder LLC (57) ABSTRACT

A system and method for delivery of selected electrical impulses to selected locations on the body of a patient. In certain embodiments, the selected electrical impulses mimic the natural impulses that travel along neurons and the inverse thereof. A system for administering the selected electrical impulses may include an input element, impulse generator, impulse shaper, circuit booster element, output control element, time and sequence controller, display element, power source, and output element.

11 Claims, 6 Drawing Sheets

SYSTEM AND METHODS FOR PRODUCING AND DELIVERING ELECTRICAL IMPULSES

This application claims the benefit of U.S. Provisional Application Nos. 61/372,407 and 61/372,356 filed Aug. 10, 2010, the contents of which are incorporated herein by reference.

FIELD OF THE INVENTION

The present invention relates to a system and methods for producing certain electrical impulses and, more particularly, to delivering such electrical impulses to specific parts of a patient to treat a symptom or an ailment.

BACKGROUND OF THE INVENTION

Acupuncture practitioners have developed various conventional medical techniques for treating patients. One such technique includes manipulation and insertion of needles into locations on the body of a patient, usually a human. This technique is typically practiced by inserting needles in accord with principles of traditional Chinese Medicine. The needles typically are made of stainless steel wire and generally vary in length between 0.51 to 5.1 inches and diameter between 0.006 inches and 0.018 inches. Shorter needles are inserted near the face and eyes. Longer needles are inserted in areas that include a lot of muscle. The thickness of the needle is determined based on the patient.

In Traditional Chinese Medicine, the location of the needle insertion is determined according to four diagnostic methods, including 1) inspection, 2) auscultation and olfaction, 3) inquiring, and 4) palpation. Inspection method includes analysis of the tongue for size, shape, tension, color, and coating, and teeth marks. Auscultation and olfaction method, respectively, refer to listening for particular sounds and perceiving body odor. Inquiring method includes "seven inquiries", which are: chills and fever; perspiration; appetite, thirst, and taste; defecation and urination; pain; sleep; and menses and leukorrhea. Palpation method includes feeling the body for tender "ashi" points, left radial pulse, right radial pulse, Cun (proximal to wrist crease), Guan (one finger breadth proximal from wrist crease), and Chi (two finger breadth proximal from the wrist crease).

Traditional Chinese Medicine also teaches that a body includes channels such as energy channels, which are commonly termed meridians. The treatment needle is placement according to the location of certain meridians.

Certain disadvantages associated with needle-based therapy include pain at the site of needle insertion, fear of needles, and inconvenience of leaving needles in place for several days in some therapies.

Another method of acupuncture includes application of electric pulses to the skin of a patient at locations selected in accordance with the principles of acupuncture but without using needles that pierce the skin. Certain types of electrical pulse therapy have long been used in medicine to treat pain and other conditions. One of the forms of electrical pulse therapy is Transcutaneous Electrical Stimulation ("TENS").

The "TENS" method is based on a hypothesis developed by the practitioners Melzack and Wallfrom 1965. They proposed that activity in coarse, afferent verve fibers (A-beta-fibers that convey pressure, touch, and vibration) inhibits impulse transmission in pain pathways at spinal cord level. The coarse nerve fibers have a low threshold for electrical stimulation and are therefore simple to activate by stimulation using electrodes placed on the skin. Stimulation frequencies of 20-120 Hz may be used for conventional TENS.

In recent years, Percutaneous Electrical Nerve Stimulation ("PENS") has been used and investigated for the management of acute and chronic pain syndromes. PENS therapy utilizes needle-like electrodes placed in the soft tissues to stimulate peripheral sensory nerve at the dermatomal level corresponding to a local pathology.

PENS and TENS generally operate through different mechanisms of pain interruption along the ascending nociceptive pathways, namely, at peripheral, spinal segmental, and supraspinal. On the peripheral level, PENS stimulates mainly the pinprick A-delta and small type III fibers to achieve its effect. TENS stimulates mainly the A-beta and large type I fibers to achieve its effect. On the spinal level, the effect of PENS is mediated via the inhibitory enkephalinergic stalked cells in lamina II of the spinal grey matter. TENS is effectively mediated via interneurons with GABA receptors in the spinal cord which stimulate the inhibitory neurons. On the supraspinal level, PENS activates pituitary mechanisms releasing enkephalins and produces analgesia throughout the body. Conventional TENS are mostly segmental not involving pituitary mechanisms, and the analgesic effect is only segmental.

In clinical applications, PENS therapy seem to be significantly more effective than TENS therapy. Studies comparing PENS and TENS therapies tend to show that PENS was more effective in improving function, pain, physical activity of sleep. PENS therapy also appears to be preferred by more patients.

PENS therapy has been found to be effective in the management of pain associated with a number of conditions, including acute herpes, the prevention and management of migraine headaches, and cancer pain secondary to bone metastases. PENS therapy has been also found effective for many conditions including, but not limited to, Irritable Bowel Syndrome and dysmenorrheal.

Generally, a PENS therapeutic procedure may be performed in clinic by a pain specialist, typically, by physiatrist, anesthesiologist, or acupuncturist. A patient is usually placed on a table, when two or more electrodes are inserted in the back and around the spine, according to the location of the pain. Needle electrodes are kept in place for 30 minutes to 1 hour, while receiving an alternating electrical current generated at frequencies typically from several to 100 Hz.

Typically, the actual electrical current running through the electrodes is very small. More specifically, the current is typically administered in milliamperes. Such systems permit the electrodes to emit variable frequencies and intensities. Needle electrodes may be inserted perpendicular to the skin at variable depths, depending on the area, patient's anatomy, and the etiology of pain; typically the needles are inserted anywhere from several millimeters to several centimeters deep. Electrical clips with electrical wires are attached to the electrodes before an electrical stimulator is turned on.

These conventional methods of acupuncture have numerous limitations and disadvantages including risk of infection, skin damage, irritation, improper insertion, or additional pain. Therefore, there exists a need for improvement in the delivery of an electrical impulse to a patient.

SUMMARY OF THE INVENTION

The present invention relates to the field of electrical therapy for treating ailments. More particularly, the present invention relates to electro-acupuncture and electrical nerve stimulation therapy without the use of needles. The system according to one embodiment of the present invention is specifically designed to be able to produce an impulse identical to that generated in the human body, such as that found in the nodes of Ranvier. However, the present system may modify this impulse by adding an identical inverse of the impulse generated in the human body, before emitting the final impulse. Such impulses, comprising the portion analogous to that naturally occurring in a human body and an added identical inverse are generated with the present system and then used to stimulate organs as desired.

Generally, neurons are considered the functional unit of the nervous system of an organism and carry nerve impulses from the body to the brain and from the brain to the body. There are three basic types of neurons. Motor neurons carry impulses to and from muscles. Sensory neurons carry impulses from receptor cells to the spinal cord. Intermediate neurons connect motor and sensory neurons together in the central nervous system.

A neuron is comprised of dendrites, a cell body containing a nucleus, and an axon. Neurons permit the sending and receiving of signals through electrical impulses sometimes called action potentials. In many organisms, portions of an axon are surrounded by a myelin sheath, which insulates the axon. The myelin sheath is made of a fatty substance, which protects and insulates the axon and permits impulses to be transmitted more quickly between the sections of myelin sheath. The gaps between the myelin sheath are called nodes of Ranvier. An impulse that naturally occurs along a neuron travels from node to node along an axon. Nodes of Ranvier generally occur at one millimeter intervals along the length of the axon.

For a nerve impulse to occur, a neuron needs to be stimulated to such a level that the cell depolarizes. When a portion of the axon is depolarized, ions flow in and out of the axon to cause a relative change in its polarity. In the resting state, a neuron has a negatively charged interior relative to outside the cell. Upon stimulation of the neuron, a nerve impulse moves along the axon by the stimulation of subsequent areas due to the action potential of the adjacent.

As such, the generation and delivery of impulses that mimic the frequency and intensity of neuron impulses is beneficial since cells are prepared to receive these impulses.

The system of the present invention generates such impulses in an improved and modified form. The present system is operable in up to four modes known in the field of electro-acupuncture: 1) sedation, 2) tonification, 3) immune system stimulation, and 4) electro-muscle stimulation. The first three modes use the novel impulse comprised of the portion mimicking the impulse found in the human body immediately followed by its identical inverse. The two parts together are hereinafter referred to as an impulse pack. Thus, the present invention not only generates the impulse found in the human body but also improves its efficacy by adding on its identical inverse, to form an impulse pack.

In the second mode, impulse packs are emitted for 0.5 seconds, then paused for 0.5 seconds. This is repeated for the desired duration determined by the administrator of the procedure.

In the third mode, three sets having 15 impulse packs each are emitted with 0.5 second pauses between each 15 impulse pack set, followed by a 45 second pause before the next 3 sets are sent.

In the fourth mode, impulses commonly used for electro-muscle stimulation may be used. In this mode, two sets of sinusoidal modulated impulses are emitted for 0.5 seconds with a 0.5 second pause between each set. The fourth mode is administered using known methods of electro-muscular stimulation.

Embodiments of a system according to the present invention may include a system including an input element, impulse generator, impulse shaper, time and sequence controller, output element, output control element, circuit booster element, and a display element. Certain embodiments also include a computer. Embodiments of a system according to the present invention are configurable to generate and deliver impulse packs in selected modes. The modes are selected to include the most efficient and least harmful treatment. The term "treatment" includes all the impulses administered to a patient to treat an ailment or provide a therapy. A treatment may include impulse packs delivered in a single day or over a series of days.

In a preferred embodiment, the system will generate an impulse pack that includes a mimic impulse, an impulse that mimics the frequency and intensity of an impulse that occurs naturally in the nodes of Ranvier and runs along the nodes of Ranvier found in a neuron of an organism, specifically a human. An impulse that occurs naturally in the neuron of an organism is termed a "neuron impulse" for purposes of this application. An impulse that mimics a neuron impulse is termed a "mimic impulse" for purposes of this application. Mimic impulses generally are effective and more acceptable to the human body than artificial electrical impulses that are not the same as or similar to neuron impulses. The impulse pack also includes an impulse that is the identical inverse of the mimic impulse, which is termed an "inverse impulse." In a preferred embodiment, an impulse pack includes a mimic impulse immediately followed by an inverse impulse. The delivery of this novel two-part impulse is beneficial and essential in the management of symptoms, ailments and various other conditions because such an impulse is safer and less burdensome on the cells and cell membranes.

The present invention and its attributes and advantages will be further understood and appreciated with reference to the detailed description below of presently contemplated embodiments, taken in conjunction with the accompanying drawings.

DETAILED DESCRIPTION OF EMBODIMENTS
OF THE INVENTION

Figure 1A:
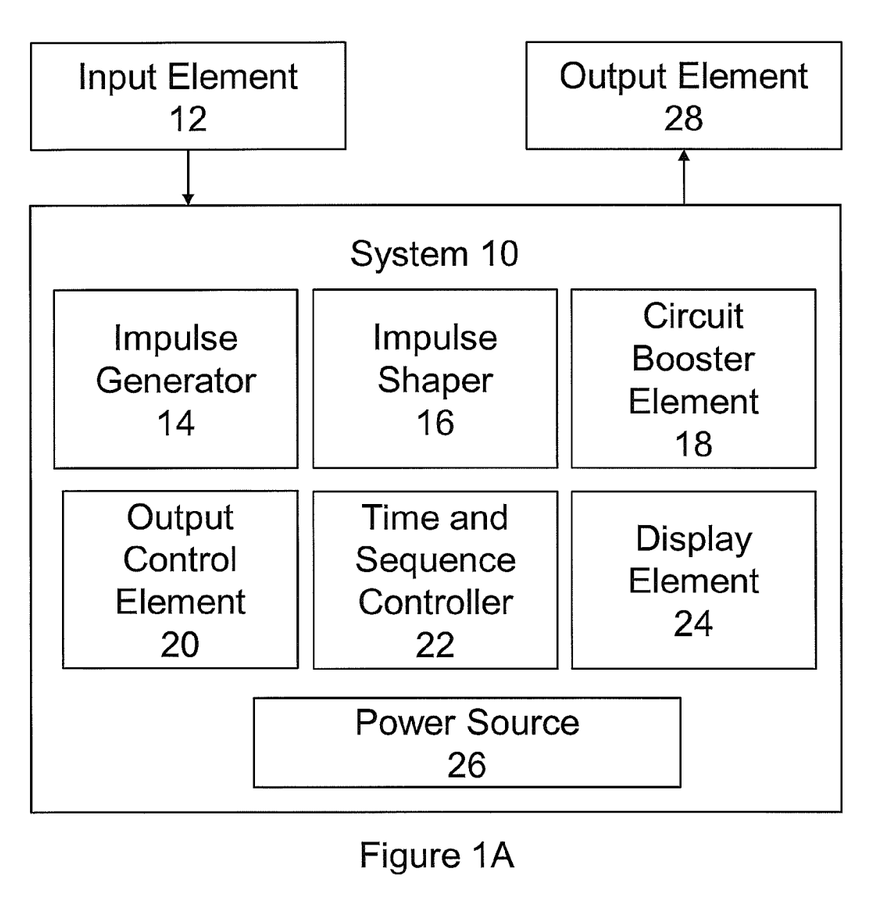
FIG. 1A illustrates an embodiment of a system for generation and delivery of impulse packs.
Figure 1B:
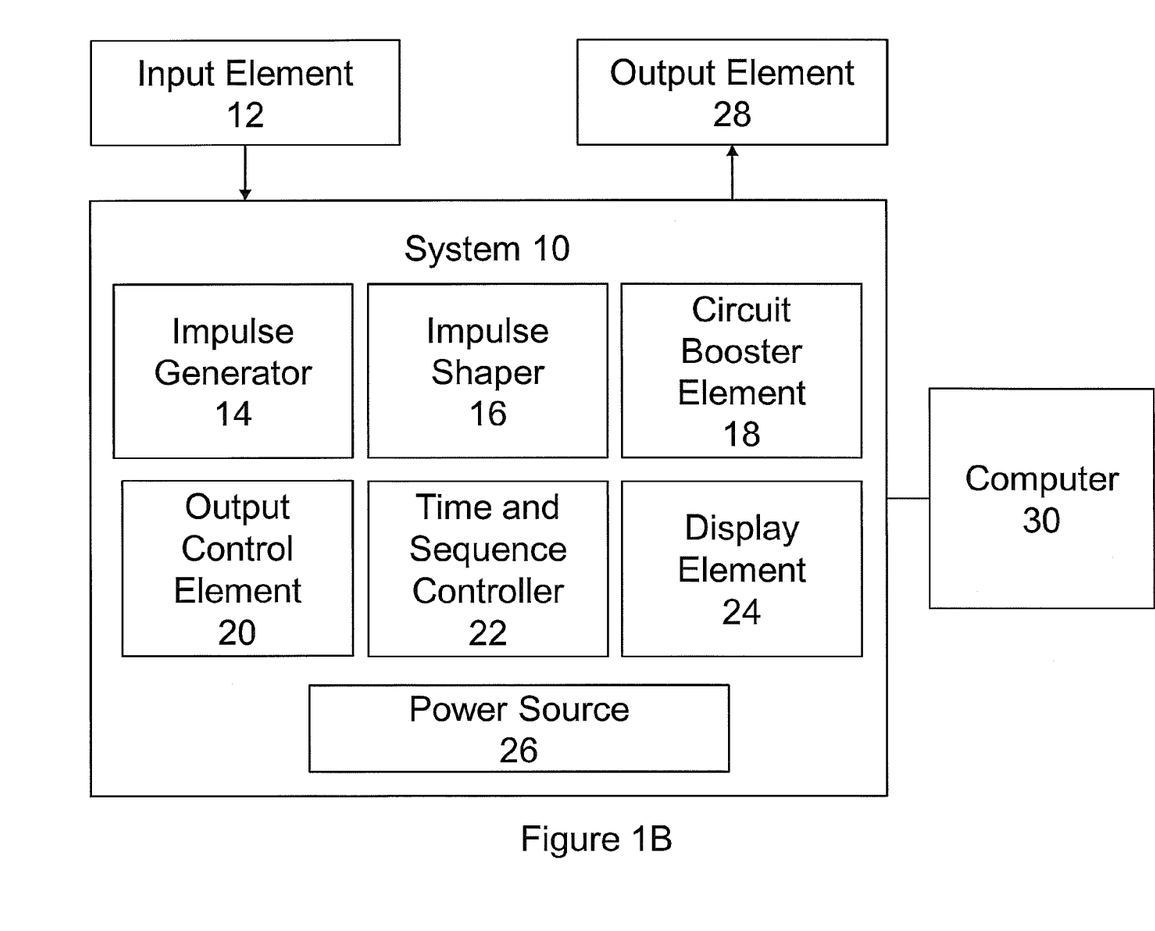
FIG. 1B illustrates an alternative embodiment of a system for generation and delivery of impulse packs.
Figure 4:
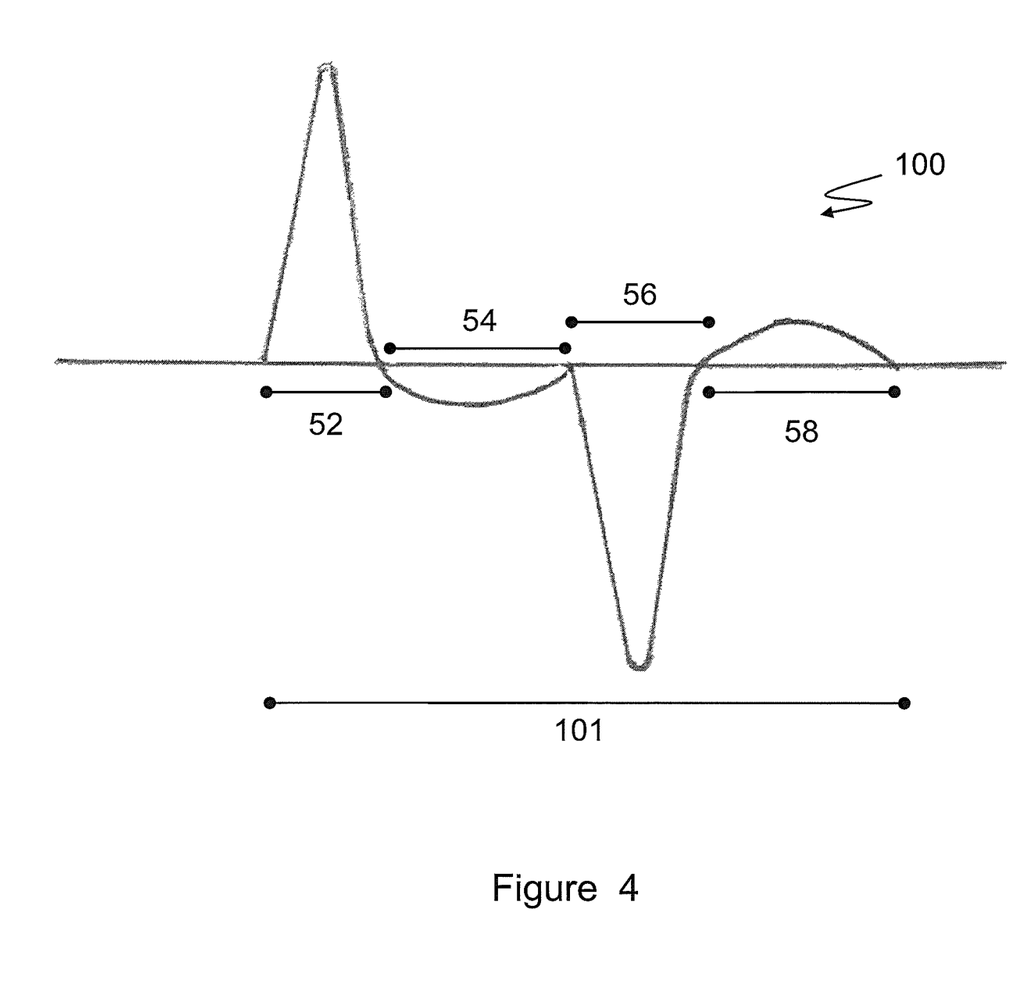
FIG. 4 illustrates an impulse pack according to the present invention.

As illustrated in FIG. 1A, embodiments of a system 10 according to the present invention may include an input element 12, impulse generator 14, impulse shaper 16, circuit booster element 18, output control element 20, time and sequence controller 22, display element 24, power source 26, and output element 28. As illustrated in FIG. 1B, an embodiment of the present invention may also include a computer 30. Embodiments of an input element 12 may include contactors typically used in EKG. Embodiments of an impulse generator 14 are configured to be capable of generating an impulse according to the present invention. Embodiments of an impulse shaper 16 are configured to control the shape of an impulse 100 including the amplitude. The impulse shaper 16 is capable of creating impulses 100 shaped as shown in FIG. 4.

Embodiments of a circuit booster element 18 include a power converter with an output of Direct Current ("DC") voltage greater than its input DC voltage. Such a circuit booster element 18 may include two semiconductor switches (for example, a diode and a transistor) and at least one energy storage element. Certain embodiments also may include capacitors, which may be added to the output of the converter to reduce output voltage ripple. Embodiments of an output control element 20 are configured to control the impulse 100. Embodiments of time and sequence controller 22 include elements that permit a user to control the time and sequence of the impulses 100.

Embodiments of the display element 24 are configured to display information regarding the system 10 including, for example, information regarding input into the system 10 and output such as an impulse 100 emitted from the system 10.

Embodiments of a power source 26 include any source capable of powering the system 10 to emit impulses 100 in the selected mode(s). In certain embodiments, a power source 26 is a 9-volt battery.

Embodiments of an output element 28 may include any component capable of delivering an electrical impulse to a patient. Certain embodiments of an output element 28 include an electrode, a rod, or a probe.

Figure 2:
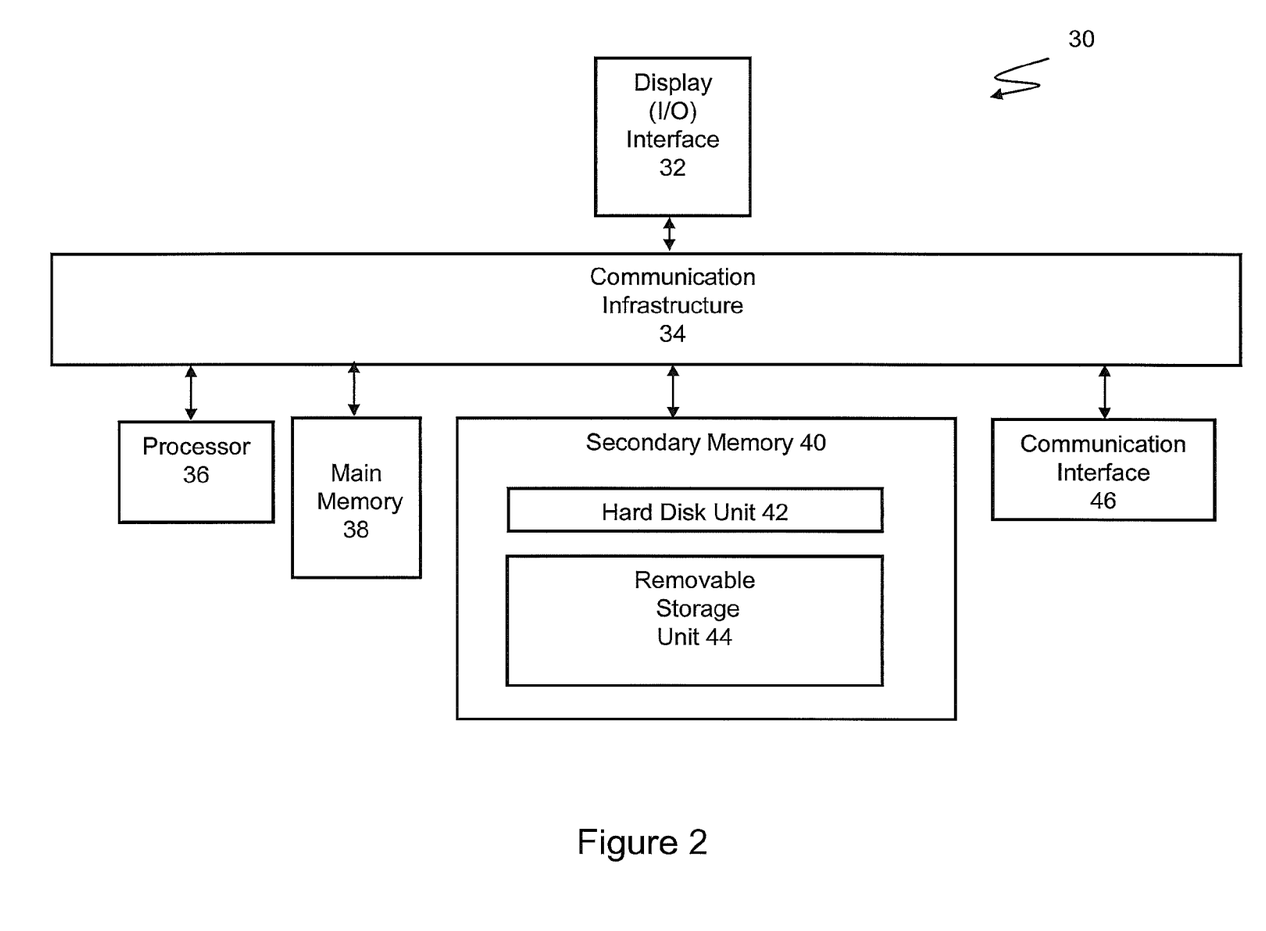
FIG. 2 illustrates an exemplary computing system that may be used to implement the system and methods according to the invention.

FIG. 2 illustrates an exemplary computing device 30 that may be used to implement the system and methods according to the invention. One or more computing devices 30 may carry out the methods presented herein as computer code.

Computing device 30 may include an input/output display interface 32 connected to communication infrastructure 34—such as a bus—through which data, such as graphics, text, and information, may be forwarded from the communication infrastructure 34 or from a frame buffer (not shown) to other components of the computing device 30. The input/output display interface 32 may be, for example, a keyboard, touch screen, joystick, trackball, mouse, monitor, speaker, printer, any other computer peripheral device, or any combination thereof, capable of entering and/or viewing data.

Computing device 30 includes one or more processors 36, which may be a special purpose or a general-purpose digital signal processor that processes certain information. Computing device 30 also includes a main memory 38, for example random access memory ("RAM"), read-only memory ("ROM"), mass storage device, or any combination thereof. Computing device 30 may also include a secondary memory 40 such as a hard disk unit 42, a removable storage unit 44, or any combination thereof. Computing device 30 may also include a communication interface 46, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, etc.

It is contemplated that the main memory 38, secondary memory 40, communication interface 46, or a combination thereof, function as a computer usable storage medium, otherwise referred to as a computer readable storage medium, to store and/or access computer software including computer instructions. For example, computer programs or other instructions may be loaded into the computing device 30 such as through a removable storage device, for example, a floppy disk, ZIP disks, magnetic tape, portable flash drive, optical disk such as a CD or DVD or Blu-ray, Micro-Electro-Mechanical Systems ("MEMS"), nanotechnological apparatus. Specifically, computer software including computer instructions may be transferred from the removable storage unit 44 or hard disc unit 42 to the secondary memory 40 or through the communication infrastructure 34 to the main memory 38 of the computing device 30.

Communication interface 46 allows software, instructions and data to be transferred between the computing device 30 and external devices or external networks. Software, instructions, and/or data transferred by the communication interface 46 are typically in the form of signals that may be electronic, electromagnetic, optical, or other signals capable of being sent and received by the communication interface 46. Signals may be sent and received using wire or cable, fiber optics, a phone line, a cellular phone link, a Radio Frequency ("RF") link, wireless link, or other communication channels.

Computer programs, when executed, enable the computing device 30, particularly the processor 36, to implement the methods of the invention according to computer software including instructions.

The computing device 30 described herein may perform any one of, or any combination of, the steps of any of the methods presented herein. It is also contemplated that the methods according to the invention may be performed automatically, or may be invoked by some form of manual intervention.

The computing device 30 of FIG. 2 is provided only for purposes of illustration, such that the invention is not limited to this specific embodiment. It is appreciated that a person skilled in the relevant art knows how to program and implement the invention using any computing device 30.

Figure 3:
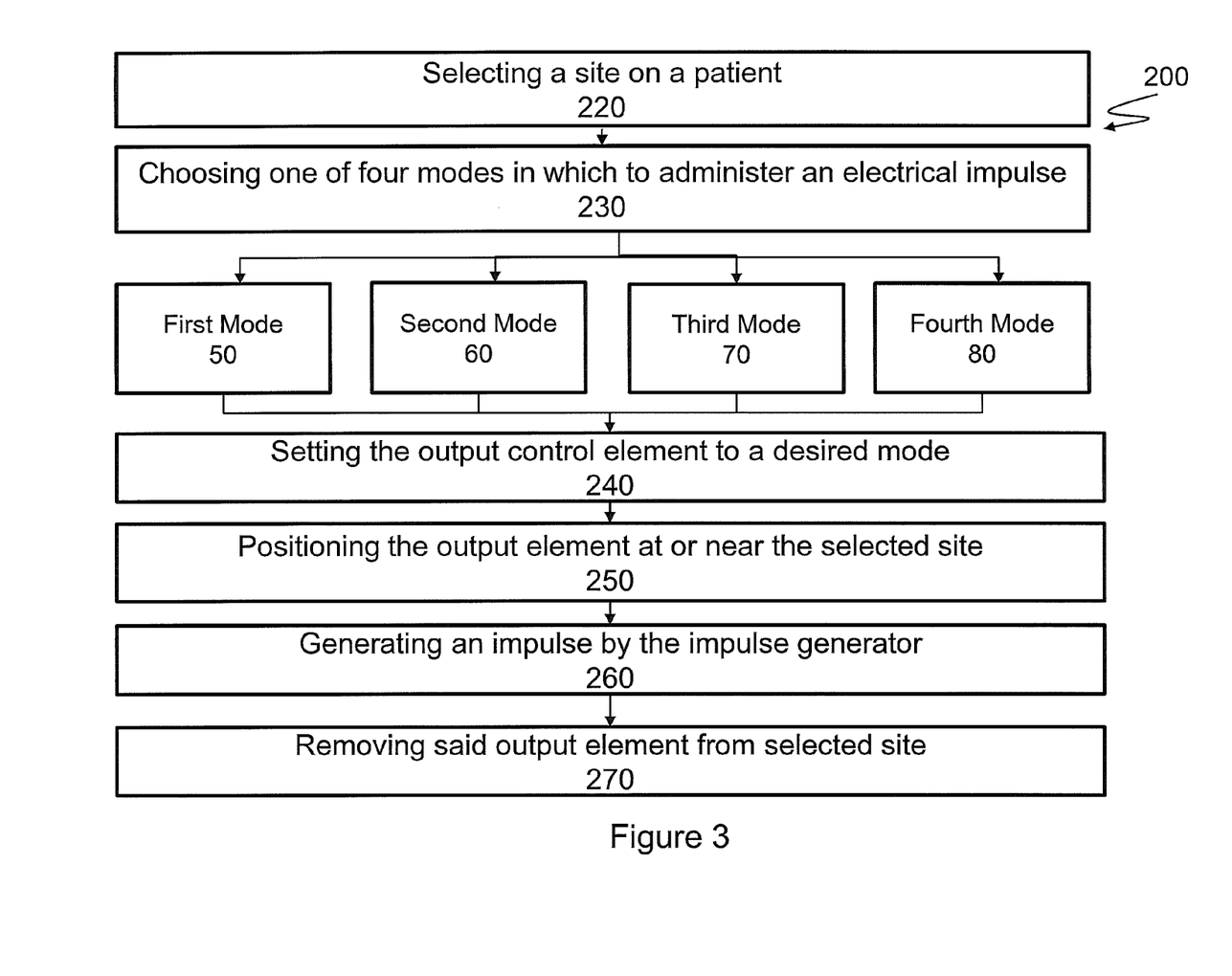
FIG. 3 illustrates a method of producing and delivering of an impulse to a patient.

Embodiments of the system 10 of the present invention are configured to emit impulses 100 in various modes. FIG. 3 illustrates one embodiment of a method 200 for administering impulse packs 101 using a system 10. One embodiment of the method 200 includes the steps of selecting a site on the body of a patient 220; choosing one of four modes 230 in which to administer an electrical impulse: first mode 50, second mode 60, third mode 70, or fourth mode 80; setting the output control element to a desired mode 240, positioning the output element at or near the selected site 250, generating an impulse by the impulse generator 260; and removing the output element from the selected site 270.

FIG. 4 illustrates a graphical representation of an impulse pack 100 as may be used in first mode 50, second mode 60, or third mode 70 of the exemplary system 10. An embodiment of an impulse pack 101 includes a first segment 52, a second segment 54, a third segment 56, and a fourth segment 58. The first segment 52 and the second segment 54 represent a mimic impulse that reproduces the neuron impulse found in the human body. The third segment 56 and fourth segment 58 represent an inverse impulse. Together, the first segment 52, second segment 54, third segment 56, and fourth segment 58 form an impulse pack.

In the first mode 50, the impulse pack 100 is preferably emitted as follows: first segment 52 and third segment 56 last 50 microseconds, and second segment 52 and a fourth segment 58 last approximately 100 microseconds. In the preferred embodiment of the impulse pack, the impulse pack has a rise time of 10-15 microseconds and a fall time of 100-120 microseconds. According to the preferred embodiment, the frequency of the impulse 100 is 1100 Hertz. The amplitude is up to 150 v, and varies depending on the patient and his tolerance or threshold. When the patient advises that he feels the impulse, the limit is set. For example, older patients or patients with dry skin may have more resistance and require higher voltage. Conversely, patients with moister skin will have lower resistance and may require only about 50-70 v amplitude.

Figure 5A:
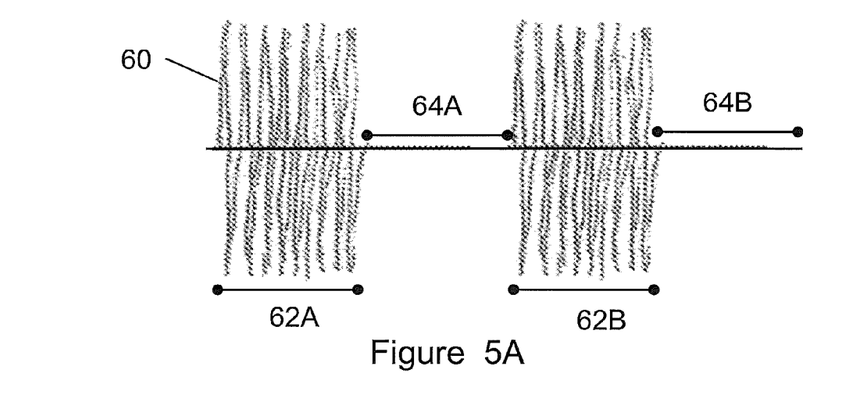
FIG. 5A illustrates a second mode.
Figure 5B:
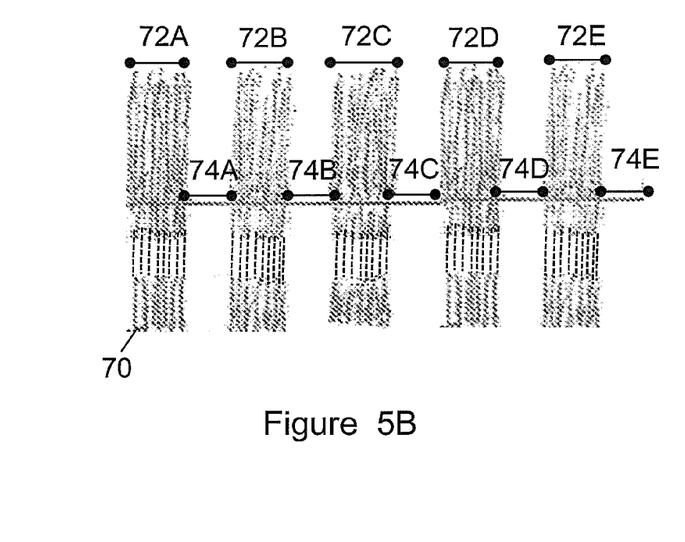
FIG. 5B illustrates a third mode.
Figure 5C:
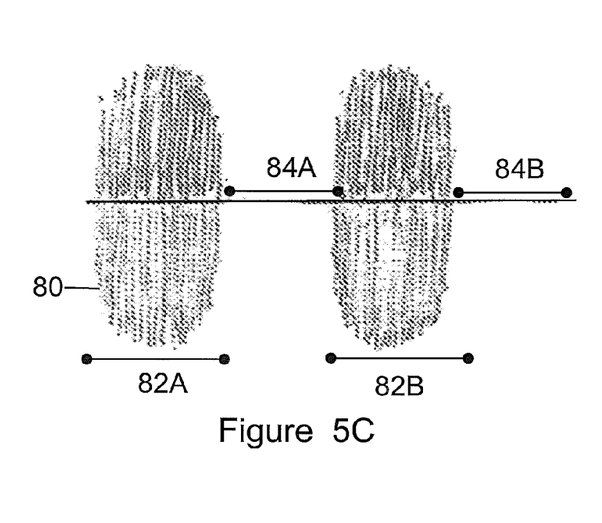
FIG. 5C illustrates a fourth mode.

FIG. 5 illustrates a graphical representation of the second mode 60, third mode 70, and fourth modes 80 in FIGS. 5A, 5B, and 5C, respectively, of a system 10 according to the present invention.

More specifically, FIG. 5A illustrates a representation of an embodiment of impulse packs 101 in a second mode 60. An embodiment of a second mode 60 includes a first part 62A, a second part 64A, a third part 62B, and a fourth part 64B. In the first part 62A and third part 62B, impulse packs 101 are emitted for 0.5 seconds. The second part 64A and fourth part 64B include a time period of 0.5 seconds in which no impulse 100 is emitted.

FIG. 5B illustrates a representation of an embodiment of impulse packs 101 in a third mode 70. An embodiment of a third mode 70 includes a first section 72A, second section 74A, third section 72B, fourth section 74B, fifth section 72C, sixth section 74C, seventh section 72D, eighth section 74D, ninth section 72E, and tenth section 74E. During the first section 72A, third section 72B, fifth section 72C, seventh section 72D, and ninth section 72E, fifteen impulse packs 101 are emitted in approximately fifteen seconds. The second section 74A, fourth section 74B, sixth section 74C, eighth section 74D, and tenth section 74E represent a time period of forty-five seconds in which no impulse is emitted. The third mode 70 may be emitted for five minutes or less.

FIG. 5C illustrates a graphical representation of an embodiment of impulse packs 101 in a fourth mode 80. An embodiment of a fourth mode 80 includes a first portion 82A, second portion 84A, third portion 82B, and fourth portion 84B. A first portion 82A and a third portion 82B include sinusoidal modulated impulses emitted for 0.5 seconds. A second portion 84A and fourth portion 84B is a time period of approximately 0.5 seconds in which no impulse is emitted. The fourth mode 80 is administered using known methods of electro-muscular stimulation.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

What is claimed is:

1. A system for producing and administering an electrical impulse to a patient, comprising:
    an impulse generator to generate the electrical impulse, wherein the electrical impulse is an impulse pack including a first segment, a second segment, a third segment, and a fourth segment, the first segment and the second segment representing a mimic impulse that reproduces the neuron impulse found in the human body, the third segment and the fourth segment representing an inverse impulse that is the inverse of the mimic impulse;
    an output element configured to be positioned on skin of the patient to deliver the electrical impulse;
    an output control element to control the frequency of the electrical impulse;
    a display element to display information regarding the system; and
    a power source.

2. The system for producing and administering an electrical impulse to a patient according to claim 1, wherein a plurality of electrical impulses are delivered to the patient in succession with each electrical impulse of the plurality being of the same amplitude.

3. The system for producing and administering an electrical impulse to a patient according to claim 1, wherein a first set of electrical impulses are delivered to the patient for a half second, followed by a half second of no electrical impulse emission delivered to the patient, followed by a second set of electrical impulses delivered to the patient for a half second, each electrical impulse of the first set of electrical impulses is of the same amplitude and each electrical impulse of the second set of electrical impulses is of the same amplitude.

4. The system for producing and administering an electrical impulse to a patient according to claim 1, wherein a first set of electrical impulses are delivered to the patient for a half second, followed by a half second of no electrical impulse emission delivered to the patient, followed by a second set of electrical impulses delivered to the patient for a half second, each electrical impulse of the first set of electrical impulses is of a different amplitude and each electrical impulse of the second set of electrical impulses is of a different amplitude.

5. The system for producing and administering an electrical impulse to a patient according to claim 1, wherein a first set of electrical impulses are delivered to the patient for a half second, followed by a half second of no electrical impulse emission delivered to the patient, followed by a second set of electrical impulses delivered to the patient for a half second, followed by forty-five seconds of no electrical impulse emission delivered to the patient, each electrical impulse of the first set of electrical impulses is of a different amplitude and each electrical impulse of the second set of electrical impulses is of a different amplitude.

6. The system for producing and administering an electrical impulse to a patient according to claim 1, wherein the first segment has a rise time of between 10 and 15 microseconds, the second segment has a fall time between 100 and 120 microseconds, the third segment has a fall time of between 10 and 15 microseconds, and the fourth segment has a rise time between 100 and 120 microseconds.

7. The system for producing and administering an electrical impulse to a patient according to claim 1, wherein the frequency of the electrical impulse is in a range from approximately 150 Hertz to approximately 1500 Hertz.

8. The system for producing and administering an electrical impulse to a patient according to claim 7, the frequency of the electrical impulse is 1100 Hertz.

9. The system for producing and administering an electrical impulse to a patient according to claim 1, further comprising an impulse shape to control the shape of the electrical impulse including the amplitude.

10. The system for producing and administering an electrical impulse to a patient according to claim 1, further comprising a time and sequence controller to control the time and sequence of the electrical impulse.

11. A system, comprising:
    means for producing a plurality of electrical impulses, each electrical impulse having a frequency of approximately 1100 Hertz and each electrical impulse comprising a mimic impulse with a rise time between 10-15 microseconds and a fall time between 100-120 microseconds and an inverse impulse with a fall time between 10-15 microseconds and a rise time between 100-120 microseconds;
    means for delivering the plurality of electrical impulses;

means for controlling output of the plurality of electrical impulses;
means for boosting voltage in a circuit;
means for inputting the plurality of electrical impulses; and
means for powering the circuit.

\* \* \* \* \*